US00PP19279P2

(12) United States Plant Patent
Vandenberg

(10) Patent No.: US PP19,279 P2
(45) Date of Patent: Oct. 7, 2008

(54) *CHRYSANTHEMUM* PLANT NAMED 'YELLOW SHARP'

(50) Latin Name: *Chrysanthemum×morifolium*
Varietal Denomination: Yellow Sharp

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 203 days.

(21) Appl. No.: 11/417,359

(22) Filed: May 3, 2006

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Yellow Sharp', characterized by its upright plant habit; dark green-colored foliage; freely and uniformly flowering habit; quilled decorative-type inflorescences that are about 5.5 cm in diameter with bright yellow-colored ray florets and green-colored centers; strong peduncles; and good postproduction longevity.

1 Drawing Sheet

Botanical classification: *Chrysanthemum×morifolium.*
Cultivar denomination: 'Yellow Sharp'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Yellow Sharp'.

The new *Chrysanthemum* is a product of a planned breeding program conducted by the Inventor in Salinas, Calif. and Bogota, Colombia. The objective of the program is to create and develop new cut *Chrysanthemum* cultivars having inflorescences with desirable floret coloration and good inflorescence form and substance.

The new *Chrysanthemum* is a naturally-occurring whole plant mutation of the *Chrysanthemum×morifolium* cultivar Sharp, disclosed in U.S. Plant Pat. No. 13,439. The new *Chrysanthemum* was discovered and selected by the Inventor as a single flowering plant within a population of plants of the cultivar Sharp in November, 2002, in Bogota, Colombia. The selection of this plant was based on its desirable inflorescence color and good form and substance.

Asexual reproduction of the new *Chrysanthemum* by terminal cuttings in a controlled environment in Bogota, Colombia since February, 2003, has shown that the unique features of this new Chrysanthemum are stable and reproduced true to type in successive generations.

SUMMARY OF THE INVENTION

Plants of the cultivar Yellow Sharp have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yellow Sharp'. These characteristics in combination distinguish 'Yellow Sharp' as a new and distinct cultivar of *Chrysanthemum:*

1. Upright cut *Chrysanthemum* that is usually grown as a naturally spray.
2. Dark green-colored foliage.
3. Freely and uniformly flowering habit.
4. Quilled decorative-type inflorescences that are about 5.5 cm in diameter with bright yellow-colored ray florets and green-colored centers.
5. Response time about 63 days.
6. Strong peduncles.
7. Good postproduction longevity with inflorescences and foliage maintaining good substance and color for about two weeks in an interior environment.

Plants of the new *Chrysanthemum* differ from plants of the parent, the cultivar Sharp, in the following characteristics:

1. Plants of the new *Chrysanthemum* flower slightly later than plants of the cultivar Sharp.
2. Plants of the new *Chrysanthemum* and the cultivar Sharp differ in ray floret color as ray florets of plants of the cultivar Sharp are white in color.

Plants of the new *Chrysanthemum* can be compared to plants of the *Chrysanthemum* cultivar White Yoneedle, disclosed in U.S. Plant Pat. No. 18,135. In side-by-side comparisons conducted in Bogota, Colombia, plants of the new *Chrysanthemum* differed from plants of the cultivar White Yoneedle in the following characteristics:

1. Plants of the new *Chrysanthemum* had smaller inflorescences than plants of the cultivar White Yoneedle.
2. Plants of the new *Chrysanthemum* and the cultivar White Yoneedle differed in ray floret color as plants of the cultivar White Yoneedle had white-colored ray florets.
3. Plants of the new *Chrysanthemum* had shorter peduncles than plants of the cultivar White Yoneedle.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering stem of 'Yellow Sharp' grown as a natural spray.

The photograph at the top of the sheet comprises a close-up view of typical inflorescences of 'Yellow Sharp' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Oxnard, Calif. during the winter and spring in a polyethylene-covered greenhouse and under conditions and practices which approximate those generally used in commercial *Chrysanthemum* production. Measurements and numerical values represent averages for typical flowering plants. Plants were grown as single-stem natural spray cut *Chrysanthemums*. The photographs and measurements were taken when plants were about three months old.

Botanical classification: *Chrysanthemum×morifolium* cultivar Yellow Sharp.

Parentage: Naturally-occurring whole plant mutation of the *Chrysanthemum×morifolium* cultivar Sharp, disclosed in U.S. Plant Pat. No. 13,439.

Propagation:

*Type.*—Terminal vegetative cuttings.

*Time to initiate roots.*—About ten to 14 days with soil temperatures of about 18° C. to 21° C.

*Root description.*—Fine, fibrous; white in color.

*Rooting habit.*—Freely branching.

Plant description:

*Appearance.*—Herbaceous decorative-type cut flower that is typically grown as a natural spray.

*Flowering stem description.*—Aspect: Erect. Length: About 114 cm. Diameter: About 6 mm. Internode length: About 4 cm. Texture: Pubescent; longitudinally ridged. Color: 146C.

*Foliage description.*—Arrangement: Alternate; simple. Length: About 10.5 cm. Width: About 5.8 cm. Apex: Acuminate. Base: Attenuate. Margin: Palmately lobed; sinuses parallel to divergent. Texture, upper and lower surfaces: Pubescent; veins prominent on lower surface. Color: Developing foliage, upper surface: 147A. Developing foliage, lower surface: 146A. Fully expanded foliage, upper surface: 147A; venation, 147C. Fully expanded foliage, lower surface: 147B; venation, 148B. Petiole: Length: About 1.7 cm. Diameter: About 4 mm. Texture, upper and lower surfaces: Pubescent. Color, upper and lower surfaces: 148A to 148B.

Inflorescence description:

*Appearance.*—Decorative-type inflorescence form with quill-shaped ray florets. Inflorescences borne on terminals, arising from leaf axils. Ray and disc florets develop acropetally on a capitulum. Uniformly flowering.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 63 days later when grown as a natural spray.

*Postproduction longevity.*—In an interior environment, inflorescences and foliage will maintain good color and substance for about two weeks in an interior environment.

*Quantity of inflorescences.*—Freely flowering habit, about 16 inflorescences per stem develop. Spray width: About 15 cm.

*Inflorescence size.*—Diameter: About 5.5 cm. Depth (height): About 2.4 cm. Disc diameter: About 3 mm. Receptacle diameter: About 2.7 cm. Receptacle height: About 7 mm.

*Inflorescence buds.*—Shape: Oblate. Height: About 1.4 cm. Diameter: About 1.5 cm. Color: 2A.

*Ray florets.*—Shape: Quilled. Surface: Mostly flat. Aspect: Initially upright; when mature, about 15° from perpendicular to the peduncle. Length: About 2.8 cm. Width: About 4 mm. Apex: Emarginate. Base: Fused. Texture: Smooth, glabrous; longitudinally ridged. Number of ray florets per inflorescence: About 380 arranged in numerous rows. Color: When opening, upper surface: 11A; towards the apex, 151C, giving the green-colored center. When opening, lower surface: 11B. Fully opened, upper and lower surfaces: 11B; towards the apex, 7A; color does not fade with development.

*Disc florets.*—Shape: Tubular, elongated. Length: About 3 mm. Diameter, apex: About 1 mm. Diameter, base: Less than 1 mm. Number of disc florets per inflorescence: About six; inconspicuous. Color: Immature: Close to 1B; towards the apex, 151C. Mature: Apex: Close to 1B. Mid-section: Close to 1C. Base: Close to 145D.

*Phyllaries.*—Quantity per inflorescence/arrangement: About 58 arranged in about five whorls. Length: About 9 mm. Width: About 3 mm. Shape: Elliptic. Apex: Acute. Base: Truncate. Margin: Entire. Texture, upper surface: Smooth, glabrous. Texture, lower surface: Pubescent. Color, upper and lower surfaces: Close to 146A.

*Peduncles.*—Length: First peduncle: About 6 cm. Fourth peduncle: About 7.8 cm. Seventh peduncle: About 12.9 cm. Diameter: About 2.5 mm. Angle: About 45° from vertical. Strength: Strong. Texture: Pubescent; longitudinally ridged. Color: Close to 148A.

*Reproductive organs.*—Adroecium: Present on disc florets only. Anther shape: Rounded. Anther length: Less than 1 mm. Anther color: Close to 23A. Amount of pollen: None observed. Gynoecium: Present on both ray and disc florets. Pistil length: About 9 mm. Stigma shape: Bi-parted. Stigma color: 6A. Style length: About 7 mm. Style color: 6D. Ovary color: 155A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 4° C. and high temperatures of about 35° C.

It is claimed:

1. A new and distinct *Chrysanthemum* plant named 'Yellow Sharp' as illustrated and described.

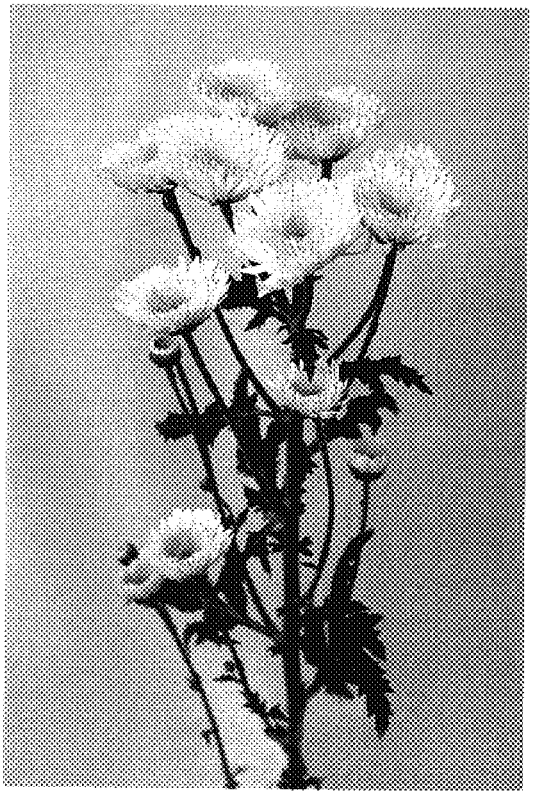
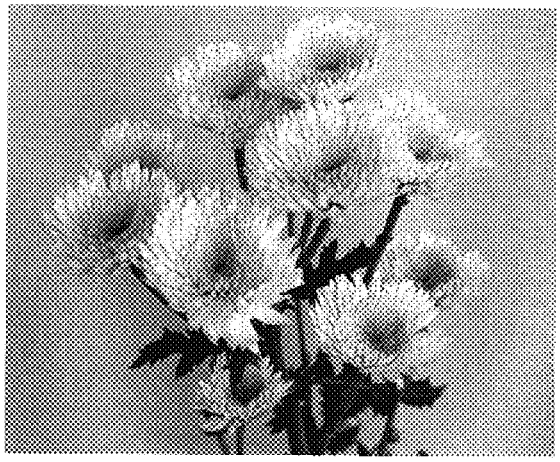

* * * * *